United States Patent [19]

Jewell

[11] Patent Number: 4,480,120

[45] Date of Patent: Oct. 30, 1984

[54] PROCESS FOR THE PREPARATION OF ALKYL-2-ALKOXYIMINO-3-OXO-4-CHLOROBUTYRATES

[75] Inventor: Linda M. Jewell, Kingsport, Tenn.

[73] Assignee: Eastman Kodak Company, Rochester, N.Y.

[21] Appl. No.: 478,588

[22] Filed: Mar. 24, 1983

[51] Int. Cl.$^3$ .................. C07C 131/00; C07C 131/02
[52] U.S. Cl. .................... 560/168; 560/121; 560/125
[58] Field of Search ............ 560/168, 121, 125

[56] References Cited

U.S. PATENT DOCUMENTS 4,205,180  5/1980  Ochiai ........................ 560/168
4,294,960  10/1981  Takaya ........................ 544/22

FOREIGN PATENT DOCUMENTS 56-127347  10/1981  Japan ........................ 560/168

Primary Examiner—Michael L. Shippen
Attorney, Agent, or Firm—Gary C. Bailey; Daniel B. Reece, III

[57] ABSTRACT

Alkyl-2-alkoxyimino-3-oxo-4-chlorobutyrates are prepared in good yield by treating an alkyl-2-alkoxyimino-3-oxobutyrate with sulfuryl chloride in the presence of a catalytic amount of a N,N-dialkyl-substituted carboxamide wherein the mole ratio of sulfuryl chloride to oxobutyrate compound is at least about 1:1, the reaction being conducted in the presence of a chlorinated aliphatic or aromatic hydrocarbon solvent at a temperature of about 10° to 50° C.

16 Claims, No Drawings

PROCESS FOR THE PREPARATION OF ALKYL-2-ALKOXYIMINO-3-OXO-4-CHLOROBUTYRATES

BACKGROUND OF THE INVENTION

This invention relates to an improved process for preparing an alkyl-2-alkoxyimino-3-oxo-4-chlorobutyrate, an intermediate in the preparation of compounds having antibacterial activity. Specifically, alkyl-2-alkoxyimino-3-oxo-4-chlorobutyrates are obtained in good yield by chlorinating alkyl-2-alkoxy-3-oxobutyrates with sulfuryl chloride in the presence of a catalytic amount of a N,N-dialkyl-substituted carboxamide.

The compounds according to the present process are useful in preparing compounds of the formula

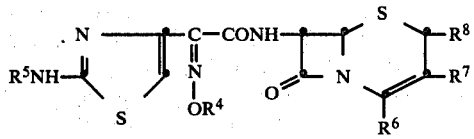

The substituents represented by $R^5$, $R^6$, $R^7$ and $R^8$ are not defined herein since they are not within the scope of my invention but are defined in various U.S. patents some of which are cited hereinbelow. The substituent $R^4$ is a part of the subject matter of my invention and will be defined hereinafter in the detailed description of my invention. Specific compounds of the above formula and the method of making same are disclosed in U.S. Pat. Nos. 4,203,899, 4,278,671 and 4,294,960. These compounds are known to have antibacterial activity against a broad spectrum of bacteria in both humans and animals.

A known method for preparing alkyl-2-alkoxyimino-3-oxo-4-chlorobutyrates using sulfuryl chloride is disclosed in the '960 patent cited hereinabove. By this process sulfuryl chloride is reacted with the appropriate oxobutyrate in acetic acid to obtain the desired chlorinated compound. This process is hampered by the need to use a complicated multistep extraction and purification procedure to isolate the final product. On a commercial scale the disadvantages of such a procedure become readily apparent, i.e., increased costs due to longer production time and use of greater amounts of reagents, additional waste streams and attendant problems in handling and disposing of the waste streams.

I have found that the chlorination of alkyl-2-alkoxyimino-3-oxobutyrates using sulfuryl chloride is improved substantially when the reaction is conducted in the presence of a catalytic amount of a N,N-dialkyl-substituted carboxamide. In particular, significantly better yields of alkyl-2-alkoxyimino-3-oxo-4-chlorobutyrates are produced through the use of catalytic amounts of a N,N-dialkyl-substituted carboxamide than when no N,N-dialkyl-substituted carboxamide is used. Moreover, the crude product may be used in unpurified form without interfering reactions from by-product contaminants, such as the dichlorinated compound alkyl-2-alkoxy-3-oxo-4,4-dichlorobutyrate.

SUMMARY OF THE INVENTION

The process of the present invention concerns an improved method for the preparation of alkyl-2-alkoxyimino-3-oxo-4-chlorobutyrates. The process involves treating an alkyl-2-alkoxyimino-3-oxobutyrate with sulfuryl chloride in the presence of a catalytic amount of a N,N-dialkyl substituted carboxamide to obtain the desired product 2-alkoxyimino-3-oxo-4-chlorobutyrate.

DETAILED DESCRIPTION

In accordance with the present process the yield of alkyl-2-alkoxyimino-3-oxo-4-chlorobutyrate prepared by treating an alkyl-2-alkoxyimino-3-oxobutyrate with sulfuryl chloride is improved substantially when the reaction is conducted in the presence of a catalytic amount of a N,N-dialkyl-substituted carboxamide.

The N,N-dialkyl-substituted carboxamides, hereinafter called carboxamides, suitable for the process of the invention are those of the formula

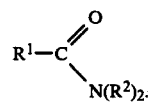

Generally, $R^1$ and $R^2$ can each independently be lower alkyls, i.e. having from one to four carbon atoms. The preferred carboxamides for my process are N,N-dimethylformamide and N,N-dimethylacetamide, with N,N-dimethylformamide being most preferred. A catalytic amount of carboxamide is employed in the reaction, that is any amount which shows a favorable comparison in the reaction as compared to the use of sulfuryl chloride alone. Ordinarily the carboxamide will be present in an amount of at least about 0.1 mole per mole of sulfuryl chloride used, with about 0.2 to 0.4 mole being preferred. While amounts less than 0.1 mole generally may be used, decreased yields of the desired 4-chloro compound will normally result.

The alkyl-2-alkoxyimino-3-oxobutyrate which may be employed in the process of my invention can be represented by the formula

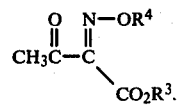

In the above formula $R^3$ and $R^4$ each generally may be any substituent which is nonreactive under the conditions of the process. Typically $R^3$ will be a branched or straight chain aliphatic hydrocarbon group having one to six carbon atoms and $R_4$ will be a branched or straight chain aliphatic hydrocarbon group having one to six carbon atoms or a cycloaliphatic hydrocarbon group having three to six carbon atoms. Exemplary aliphatic hydrocarbon substituents for $R^3$ and for $R^4$ are methyl, ethyl, n-propyl, isopropyl, n-butyl, isobutyl, t-butyl, n-pentyl, n-hexyl and the like. Exemplary cycloaliphatic hydrocarbon substituents for $R^4$ are cyclopentyl and cyclohexyl. Compounds of the above formula are generally known in the art and/or obtainable by conventional methods. A typical method of preparation is by nitrosating an alkyl oxobutyrate with sodium nitrite followed by alkylating with a suitable alkylating agent such as a dialkylsulfate.

The amount of sulfuryl chloride employed generally will be at least 1 mole per mole of oxobutyrate used. Preferably, a slight excess of sulfuryl chloride is used so that about 1.2 to 2.0 moles are used per mole of oxobutyrate. A mole ratio of about 1.3 to 1.5 of sulfuryl chloride per mole of oxobutyrate is most preferred.

The reaction process is usually most conveniently carried out in the presence of an inert solvent. Solvents which are generally suitable for my process are the inert halogenated organic solvents, particularly the chlorinated aliphatic or aromatic hydrocarbons. Examples of the chlorinated aliphatic hydrocarbons are methylene chloride, ethylene dichloride, chloroform, carbon tetrachloride, methylchloroform and the like. Examples of the chlorinated aromatic hydrocarbons are chlorobenzene, dichlorobenzene, trichlorobenzene and the like. The amount of solvent used is not critical to the process. Normally, about 1 to 10 parts of solvent per part of oxobutyrate by weight will be suitable. Of course larger amounts of solvent may be used if desired.

The reaction conditions of temperature and pressure are not particularly critical to the operation of the process. Generally, ambient temperature and pressure will be used. Because the reaction of sulfuryl chloride with the oxobutyrate is exothermic the temperature, however, will ordinarily be slightly elevated for at least a portion of the reaction period. Preferably, a reaction temperature in the range of about 10° to 50° C. and more preferably about 20°-40° C. will be maintained. Control of the reaction temperature within the desired range is normally accomplished by controlling the addition rate of the sulfuryl chloride.

A preferred embodiment of the process of the invention comprises treating ethyl-2-methoxyimino-3-oxobutyrate with sulfuryl chloride in about a 1:1.4 mole ratio in the presence of a chlorinated aliphatic hydrocarbon solvent and about 0.2 to 0.4 mole of N,N-dimethylformamide per mole of oxobutyrate to obtain crude ethyl-2-methoxyimino-3-oxo-4-chlorobutyrate. The principal by-product contaminants obtained with the crude product are unreacted starting material and the dichlorinated compound, ethyl-2-methoxyimino-3-oxo-4,4-dichlorobutyrate. The crude product is then employed, without purification or removal of existing by-products, in the preparation of syn 2-amino-α-(methoxyimino)-4-thiazole acetic acid, ethyl ester by treating the crude ethyl-2-methoxyimino-3-oxo-4-chlorobutyrate with thiourea according to established methods. The thiazole compound is then employed in the preparation of the desired antibacterial compound of the type disclosed in the U.S. patents disclosed hereinabove.

The following examples are given to further illustrate the invention, but it is to be understood that the invention is not to be limited in any way by the details described therein.

EXPERIMENTAL EXAMPLE 1

Preparation of Ethyl 2-Methoxyimino-3-Oxo-4-Chlorobutyrate in the Presence of N,N-Dimethylformamide

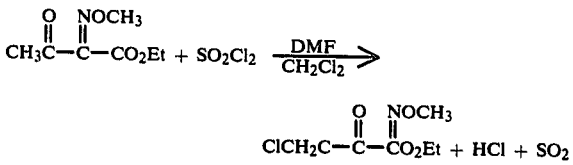

A two-liter, three-necked flask was charged with ethyl 2-methoxyimino-3-oxobutyrate (449 g, 2.59 mol), 270 ml of methylene chloride, and 72 ml of N,N-dimethylformamide. Sulfuryl chloride (494 g) was added dropwise and the reaction mixture was allowed to exotherm to 35° C. It was then stirred for 10 hours. Water (300 ml) was carefully added (it was added very slowly initially). The two layers were separated and the organic layer was stripped under reduced pressure to remove the methylene chloride. 83.7% theoretical yield; Assay: GC: 81.2%. GC analysis confirmed the presence of 1.5% of starting material and 12.0% of dichloro compound, ethyl-2-methoxyimino-3-oxo-4,4-dichlorobutyrate.

EXPERIMENTAL EXAMPLE 2

Preparation of Ethyl-2-Methoxyimino-3-Oxo-4-Chlorobutyrate in the Absence of a N,N-Dialkyl-Substituted Carboxamide The experimental procedure of Example 1 was carried out without the use of N,N-dimethylformamide, employing 20.7 g. of ethyl 2-methoxyimino-3-oxobutyrate, 50 ml. of chloroform, and 12 ml. of sulfuryl chloride. Analysis by NMR confirmed the unisolated product mixture to contain approximately 30% of chlorinated product and approximately 70% starting material.

The invention has been described in detail with particular reference to preferred embodiments thereof, but it will be understood that variations and modifications can be effected within the spirit and scope of the invention.

What is claimed is:

1. Process for the preparation of an alkyl-2-alkoxyimino-3-oxo-4-chlorobutyrate which comprises treating an alkyl-2-alkoxyimino-3-oxobutyrate with sulfuryl chloride in the presence of a catalytic amount of a N,N-dialkyl substituted carboxamide, wherein the alkyl moiety of the above alkoxyimino reactant and product is a branched or straight chain saturated aliphatic hydrocarbon having 1-6 carbon atoms and the alkyl portion of the alkoxy moiety of said reactant and product is a branched or straight chain saturated aliphatic hydrocarbon having 1-6 carbon atoms or a saturated cycloaliphatic hydrocarbon having 3-6 carbon atoms.

2. Process according to claim 1 wherein the N,N-dialkyl-substituted carboxamide is present in an amount of at least about 0.1 mole per mole of sulfuryl chloride used.

3. Process according to claim 1 wherein the N,N-dialkyl-substituted carboxamide is present in an amount of about 0.2 to 0.4 mole per mole of sulfuryl chloride used.

4. Process according to claim 1 wherein the N,N-dialkyl-substituted carboxamide is N,N-dimethylformamide or N,N-dimethylacetamide.

5. Process according to claim 1 wherein the alkyl moiety of the alkoxyimino reactant and product is methyl, ethyl, n-propyl, isopropyl, n-butyl, isobutyl, t-butyl, n-pentyl or n-hexyl and the alkyl portion of the alkoxy moiety of said reactant and product is methyl, ethyl, n-propyl, isopropyl, n-butyl, isobutyl, t-butyl, n-pentyl, cyclopentyl, n-hexyl, or cyclohexyl.

6. Process according to claim 1 wherein the reaction is carried out in the presence of a chlorinated aliphatic or aromatic hydrocarbon solvent.

7. Process according to claim 5 wherein the solvent is selected from the group consisting of methylene chloride, ethylene dichloride, chloro-form, carbon tetrachloride, methyl chloroform, chlorobenzene, dichlorobenzene and trichlorobenzene.

8. Process according to claim 1 wherein the reaction is conducted at a temperature of about 10° to 50° C.

9. Process according to claim 1 wherein the mole ratio of sulfuryl chloride to oxobutyrate reactant is at least about 1:1.

10. Process according to claim 1 wherein the mole ratio of sulfuryl chloride to oxobutyrate reactant is about 1.2–2.0:1.

11. Process for the preparation of ethyl 2-methoxyimino-3-oxo-4-chlorobutyrate which comprises treating ethyl 2-methoxyimino-3-oxobutyrate with sulfuryl chloride in the presence of a catalytic amount of a N,N-dialkyl substituted carboxamide.

12. Process according to claim 11 wherein the N,N-dialkyl-substituted carboxamide is N,N-dimethyl formamide.

13. Process according to claim 11 wherein the N,N-dialkyl-substituted carboxamide is present in an amount of at least 0.1 mole per mole of sulfuryl chloride.

14. Process according to claim 11 wherein the N,N-dialkyl-substituted carboxamide is present in an amount of about 0.2 to 0.4 mole per mole of sulfuryl chloride.

15. Process according to claim 11 wherein the reaction is carried out in the presence of a chlorinated aliphatic or aromatic hydrocarbon solvent.

16. Process according to claim 11 wherein the mole ratio of sulfuryl chloride to oxobutyrate is about 1.3–1.5:1.

* * * * *